United States Patent [19]

Slimak

[11] Patent Number: 4,911,943
[45] Date of Patent: Mar. 27, 1990

[54] PROCESSES FOR PRODUCTS FROM AMARANTH

[76] Inventor: Karen M. Slimak, 9207 Shotgun Ct., Springfield, Va. 22153

[21] Appl. No.: 824,786

[22] Filed: Jan. 31, 1986

[51] Int. Cl.$^4$ ............................................. A23L 1/214
[52] U.S. Cl. .................................... 426/629; 426/518; 426/523; 426/524; 426/551; 426/552; 426/601; 426/615; 426/661; 426/804
[58] Field of Search ................ 426/637, 640, 518, 523, 426/524, 551, 552, 601, 615, 661, 804

[56] References Cited

U.S. PATENT DOCUMENTS

| 91,554 | 6/1969 | Marshall | 426/637 |
|---|---|---|---|
| 310,927 | 1/1985 | Whitcomb | 426/637 |
| 3,881,028 | 4/1975 | Capossela et al. | 426/637 |

FOREIGN PATENT DOCUMENTS

| 1517050 | 8/1974 | Fed. Rep. of Germany . | |
| 2950315 | 6/1981 | Fed. Rep. of Germany . | |
| 3141174 | 4/1983 | Fed. Rep. of Germany . | |
| 1395654 | 2/1964 | France . | |
| 2574633 | 6/1986 | France . | |
| 104850 | 8/1980 | Japan | 426/639 |

OTHER PUBLICATIONS

Websters Third International Dictionary, P. B. Grove (Editor), Merriam Co. Publishers, pp. 384, 875 & 1866, 65 (1961).
Sanchez-Marroquin et al., "Industrial Corn Flour Enrichment with Whole Amaranth Flour", Archivos Latinoamericanos de Nutrition, 1985, 35(3), 518–535, Dialog Abstract 338213.
Casier et al., "Bread Production from Pure Flours of Tropical Starchy Crops", Trop. Foods Chem. Nutr. Inglett et editers (1979), vol. 1, pp. 279–340.
Talburt et al., "Potato Processing", Avi Publishing Co, 1959, pp. 390–391.
Weber, E. J., The Inca's Answer to Food Shortage, Nature, UK, 1978, 272 (5653), 486, entire article.
Faure, J. C., and Chatelanat, R. P., Production and Marketing of Composite Flour Bakery Goods in Developing Countries, Proceedings IV International Congress of Food Science and Technology (1974), vol. V. 231–242, entire article.
Watt, B. K., and Merrill, A. L., Composition of Foods, Agriculture Handbook, No. 8, U.S. Department of Argiculture, 1963, p. 51.
Teutonico and Knorr, Amaranth: Composition, Properties, and Applications of a Rediscovered Food Crop, Institute of Food Technologists, pp. 49–59, 120–121, Apr. 1985.
Yanez et al, Amaranthus Hypochondriacus: Starch Isolation and Partial Characterization, Cereal Chemistry, vol. 63, No. 3, pp. 273–276, May–Jun. 1986.
Sanchez-Marroquin et al, Amaranth Flour Blends and Fractions for Baking Applications, Journal of Food Science, vol. 50, No. 3, pp. 789–794, May–Jun. 1985.
Chemical Abstracts, vol. 99, No. 13, Sep. 1983, p. 485, abstract No. 103962p, Columbus, Ohio, U.S.; A. Sanchez Marroquin: "Two forgotten crops of agroindustrial importance: amaranth and quinoa", & Arch. Latinoam. Nutr. 1983, 33(1), 11–32 *abstract*.

Primary Examiner—R. B. Penland
Attorney, Agent, or Firm—Stevens, Davis, Miller & Mosher

[57] ABSTRACT

A variety of different food products, prepared from amaranth and quinoa varieties of the families, Chenopodiaceae and Amaranthaceae, are substitutes for wheat and other grains, milk, eggs, and a partial substitute for nuts.

21 Claims, No Drawings

PROCESSES FOR PRODUCTS FROM AMARANTH

BACKGROUND OF THE INVENTION (1) Field of Invention

The present invention is concerned with the utilization of seeds of the amaranth, quinoa and all other seeds from in the families Chenopodiaceae, and Amaranthaceae, with the purpose of producing various flours and other valuable edible products and industrial products.

The present invention is concerned with the utilization of flour from amaranth with the purpose of producing valuable products such as highly nutritious food products that are complete substitutes for wheat, milk, eggs, and some uses of nuts.

(2) Description of The Background

To increase the number of food products and forms of food products is of the greatest importance to persons with food allergies, and will become of even greater importance as food allergies are diagnosed in increasing numbers of people. As the potential problems of food allergies are more recognized, increasing numbers of people are looking for non-wheat items to include in their diets, to increase variety and aid in the prevention of food allergies.

Food allergies and intolerances have been known to exist for hundreds of years. The symptoms vary with each individual, and can include congestion, asthma, diarrhea, headaches, dizziness, joint pains, hives, eczema and in the most severe cases can cause anaphalaxis and even death. In recent decades, along with most other diseases related to the immune or auto-immune system, the incidence of food allergies has increased. In addition the number of foods to which a given individual reacts, and the severity of the reactions seems to be increasing. Indications are that food allergies/intolerances will continue to become increasingly more common and severe.

The need for new food sources and alternatives parallels the increase in food allergies. As the number of foods an individual can eat begins to dwindle, it becomes increasingly more difficult to maintain a nutritious well-balanced diet from the foods remaining, and the search for new foods intensifies. For many food allergy patients, the allergy problem steadily becomes more severe as the patient is unable to avoid becoming malnurished.

There is, then, a real need for alternatives to the food products that are the common and accepted staples in the American diet. These food products need to be from hypoallergenic foods so they have the best chance of being well tolerated by the greatest numbers of people. The hypoallergenic food products need to provide acceptable substitutes for the most hyperallergenic food products—wheat, corn, and other members of the grass family, legumes, milk and milk products, eggs, nuts, and yeast.

The alternative food products should be from less common or less well known foods. Such foods will have been eaten less often, if at all, and there will be a lower chance for a person to have developed allergies to the new foods. Products from such uncommon foods could probably be tolerated by most persons, and the risk of developing allergies to the foods would be low.

The alternative food products need to be developed from foods in separate food families. This is important because food allergy patients can easily develop allergies to foods that are closely related to the foods they are already allergic to. New food products from as many new food families as possible are much more needed than are food products from uncommon foods in a common food family (such as milo from the grass family). Alternative food products from food families not frequently included in peoples' diets will increase substantially the foods that people can eat in their rotation diets.

The alternative food products need to be highly concentrated foods. The above list of hyperallergenic foods includes most of the concentrated carbohydrates in the normal American diet. When people have to exclude these foods from their diets, the plant sources they have left to eat are primarily green leafy vegetables, tubers, and fruits. These food sources are high in fiber, but are relatively low in carbohydrates.

The alternative food products need to be as close to the eliminated foods as possible, in form and texture. For example, breads, pastas, cereal, cookies are needed from hypoallergenic sources, and these need to be as similar in taste and texture as possible. This will make it possible for persons to enjoy foods they are used to, and will make them more likely to stay on their diets. Also people who are concerned that they may have food allergies are more likely to seek medical treatment if they know they will have pleasant alternatives in their diets.

Alternative food products are needed that consist of one primary ingredient, and this ingredient serves to replace wheat and other grains, milk, eggs, nuts, yeast, and sugar. The food allergies of individuals vary so greatly, that as the number of ingredients in a product increases, the number of individuals that can use the product decreases. Similarly, the products need to be free of additives, preservatives, and so forth, and should be completely free of pesticides and other chemicals.

Other characteristics that are important in new food products include convenience, portability, and variety. Many patients must change their diets at a time when they are very ill, and they simply do not have the strength to perform the food preparation needed when working with fresh fruits and vegetables.

Until now there has been no alternative food product which could meet all of the above criteria. Many food products have been developed, but essentially all contain either wheat, or other grains, soy or legumes, milk, eggs, nuts, yeast, or sugar, or they don't have the characteristics of the common food products. Many specialty flours such as amaranth, have been combined with wheat flour to make new products, and these are not useful to the food allergic patient. Until now, there has been no attempt to completely replace wheat products with a non-grain flour source that also does not contain other main ingredients such as eggs, milk, sugar, and yeast.

Products of amaranth flour that are presently available are coarse, heavy, and grainy, the consistency of corn-meal-type products, which produced inferior products where the heavy flour was the primary or only ingredient other than water or oil.

It has now been found that flours having finer, more uniform particle size can be prepared that produces greatly improved products including those where amaranth flour is the primary or only ingredient other than water or oil.

SUMMARY OF THE PREFERRED EMBODIMENTS

It is one object of the present invention to provide flours and advantageous processes for producing flours from the amaranth and quinoa and all other varieties in the families Chenopodiaceae and Amaranthaceae.

Another object of the present invention to provide advantageous processes of producing valuable products from the flours of the amaranth and quinoa varieties of the family Chenopodiaceae and Amaranthaceae.

Another object of the present invention is to provide an uncooked flour product of amaranth and quinoa of family Amaranthaceae and Chenopodiaceae, having moisture content of less than 20% and retaining at least 10% of the non-farinaceous substance of the seed.

Another object of the present invention is to provide a completely or partially gelatinized flour product of amaranth and quinoa of family Amaranthaceae and Chenopodiaceae, having a moisture content of less than 20% and retaining at least 10% of the non-farinaceous substance of the seed.

Another object of the present invention is to provide edible compositions of matter from the flour of all amaranth and quinoa varieties of family, Chenopodiaceae and Amaranthaceae.

Another object of the present invention is to provide advantageous processes for producing substitutes for wheat products and other grain products.

Another object of the present invention is to provide advantageous processes for producing substitutes for milk, milk-products, and milk containing products.

Still another object of the present invention is to provide advantageous processes for producing substitutes for products containing eggs.

Still another object of the present invention is to provide advantageous processes for producing substitutes for legumes and legume-containing products.

Another object of the present invention is to provide advantageous processes for producing substitutes for nut butter products and products containing nut butters.

Another object of the present invention is to provide advantageous processes for producing substitutes for wheat, other grains, legumes, eggs, milk, and yeast-containing products using amaranth flour a essentially the only ingredient.

Still another object of the present invention is to provide novel and advantageous processes for producing the following products with amaranth flour as the only ingredient other than water, oil, salt, and baking powder: pastas, cereals, pancakes, bread, cakes, creamed cereals, cereal shreds, imitation nut butters, imitation mayonnaise, mashed potato substitutes, breads, bread crumbs, croutons, cookies, crackers, tortillas, chips, puffed chip-like products, corn bread, pie crust, pizza dough, dough-wrapped products, doughnuts, dumplings, hush puppies, pretzels, batter, milk, ice cream, milk shake, puddings, custards, light and heavy creams, condensed milk, muffins, waffles, french toast, crepes, and dry mixes for many products.

Another object of the present invention is to provide novel and advantageous processes for producing the following products with amaranth flour as a primary ingredient: pastas, cereals, pancakes, bread, cakes, creamed cereals, cereal shreds, imitation nut butters, imitation mayonnaise, mashed potato substitutes, breads, bread crumbs, croutons, cookies, crackers, tortillas, chips, puffed chip-like products, corn bread, pie crust, pizza dough, dough-wrapped products, doughnuts, dumplings, hush puppies, pretzels, batter, milk, ice cream, milk shake, puddings, custards, light and heavy creams, condensed milk, muffins, waffles, french toast, protein coating batter, crepes, and dry mixes for many products.

Another object of the present invention is to provide advantageous processes for producing infant formulas.

Another object of the present invention is to provide advantageous processes for producing pharmaceutical products that are more effective for allergy patients by the use of hypoallergenic flours such as amaranth flour as an inert ingredient.

Another object of the present invention is to provide advantageous processes for producing cosmetics containing amaranth powder as cosmetic base and facial powder, and other uses.

Briefly, these objects and other objects of the present invention as hereinafter will become more readily apparent can be attained by a plurality of method embodiments which employ a flour obtained from amaranth to prepare a variety of different foodstuffs.

DETAILED DESCRIPTION OF THE INVENTION

The word amaranth as used in this patent application is intended to include amaranth, Quiona and all other seeds of the Chenopodiaceae and Amaranthaceae families.

It has now been found that flour from amaranth ca be used in the production of many food products. Moreover the flour can be used in every way wheat flour is used, although the processes are totally different.

Amaranth is a domesticated plant that is directly descended from the pigweed. Many species and varieties exist throughout the world. Amaranth seeds and meal-type flour are used in wide numbers of products, which rely on other flours and the like to produce acceptable products. Amaranth is essentially not mentioned in the patent literature.

Quinoa seeds are 2-3 times larger than amaranth seeds, and is primarily used as a cereal product.

Products of amaranth flour that are presently available ar coarse, heavy, and grainy this is because the amaranth seeds are very hard. It was found that prolonged or repeated grinding cycles, sufficient to produce a uniformly fine flour that could be used to produce greatly improved products including those in which amaranth is the primary or only ingredient.

In the preferred embodiment, amaranth seeds are pulverized, communited and the like by any desired technique or combination of techniques common to the art to produce a meal. The particle sizes are further reduced to a moderate to fine flour by repeated steps of grinding, pulverizing, smashing, and the like, in any combination together with optional drying by any conventional method as many repetitions are needed to produce a flour to uniform moderate to fine particle size with 10-100% preferably all components of the seed remaining in the flour.

In another flour embodiment amaranth seed, meal or flour is combined with water in proportions of from 1:3 to 1:200, preferably 1:10 in any desired way and heated by any conventional means including, steam jackets and pressure, and the like under temperatures, pressure, and length of time for heating to an appropriate for the processes used, and as necessary to form a soft, gelatinized mass or mixture varying in consistency from thick paste to water. Either prior during heating or after heating, the mass is subjected to methods of pureeing, pulping, blending, comminuting, pulverizing and the like to form a smooth, homogeneous fluid or paste. This mixture is dried by suitable means of the art and pulverized to flakes or a fine or coarse powder.

In another embodiment, a dflour may be produced in the manner of the first flour embodiment, with the added step of toasting the amaranth during or before grinding.

In yet another embodiment a flour may be produced in the manner of the first embodiment, with the added step of popping the amaranth seeds before grinding o otherwise pulverizing.

A cereal substance or constituent of cereal may be prepared from the dried seeds of the amaranth which optimally may be roasted by any desired conventional technique.

A particulate material which is useful as a cereal substitute for the likes of cream of wheat can be prepared by pulverizing dried amaranth seed to particle sizes ranging from 0.3 inch to 0.02 inch, preferably 0.06 inch.

A bread product can be prepared from amaranth flour, water, and a small amount of salt (optional), oil (optional), and any conventional leavening agent in proportions ranging from 1:1/10:0 to 1:4:1 by weight, preferably 1:0.4:0.17 in processes of mixing at any desired speed, preferably a moderately high speed, shaping, and baking in any desired order or combinations of techniques common to the art. The amaranth bread is baked at temperatures ranging from 275-550 F., preferably 425 F., for 15-90 minutes, preferably 50 minutes. The bread may also be prepared with any desired combinations of conventional ingredients including but not limited to other flours, extenders, binders, fillers, preserving agents, sweeteners, flavorings, seasonings, eggs, milk, nuts, and so forth.

In still another embodiment the bread product described above, and products such as corn bread, cookies, pancakes, muffins, and the like described in examples which follow may be used to prepare bread crumb and crouton-type and other similar products.

Breads and the other products, in processes including but not limited to various orders and combinations of drying, toasting, coating, cutting, slicing, comminuting, and the like in steps conventional to the art may be used to produce bread crumb products with all possible uses of any other bread crumb products. These uses include but are not limited to: coating mixes for use alone or with batters, salad toppings, pie crusts, stuffings, and the like. They may also be prepared with any desired combinations of conventional ingredients including but not limited to other flours, extenders, binders, fillers, preserving agents, sweeteners, flavorings, seasonings, eggs, milk, nuts, and so forth.

By techniques in any desired order or combination of slicing, drying, roasting, toasting, baking, and the like, cubed products called croutons may be produced. These may be used on salads, soups, stews, stuffings, and any other ways croutons are used. The bread crumbs and croutons may also be prepared with any desired combinations of conventional ingredients including but not limited to other flours, extenders, binders, fillers, preserving agents, sweeteners, flavorings, seasonings, eggs, milk, nuts, and so forth.

In another embodiment, a corn bread- like product can be prepared from amaranth flour, water, oil, and small amounts of salt (optional), sweeteners (optional), and of any conventional leavening agents in proportions ranging from 1 : 10 : 0 to 1: 4 : 1, by weight, preferably 1 : 0.4 : 0.17 in processes of mixing at any desired speed, preferably a moderately high speed, shaping, and baking in any desired order or combinations of techniques common to the art. The amaranth corn bread is baked at temperatures ranging from 275-550 F., preferably 425 F., for 15-90 minutes, preferably 50 minutes. When a liquid sweetener such as a honey is used, the proportions range from 1 : 6 : 2 : ½ to 1 : 1/10 : 0 : 0, preferably 1 : 0.4 : 0.3 : 0.2 of amaranth flour, water, honey, and oil. The corn bread-like product may also be prepared with an desired combinations of conventional ingredients including but not limited to other flours, extenders, binders, fillers, preserving agents, sweeteners, flavorings, seasonings, eggs, milk, nuts, and so forth.

In another embodiment, a cake dough product can be prepared, in the method described above for corn bread by increasing ranges and preferred amounts: the amount of oil by 100%, increasing the amount of honey by 20%, and increasing the amount of baking powder by 25-50%. Alternatively, honey may be omitted. These doughs produce a baked cake-like product without added ingredients, although ingredients commonly used in the art may also be incorporated into the dough or added to the finished products. The cake may also be prepared with any desired combinations of conventional ingredients including but not limited to other flours, extenders, binders, fillers, preserving agents, sweeteners, flavorings, seasonings, eggs, milk, nuts, and so forth.

In still another embodiment by the processes described for corn bread products, muffins may be produced. The range of ratios of flour, water, and oil are identical to those for the corn bread product.

In another embodiment, products the likes of pancakes, doughnuts, hush puppies, batter, crepes can be prepared from combinations of amaranth flour, water, oil, and small amounts of salt (optional), sweeteners (optional), and of any conventional leavening agents in proportions. The ranges of general proportions are from 1 : ¼ : 0 to 1 : 2 : ½ with preferred proportions being 1 : 1 ½ : 1/6. These products are mixed, molded, shaped, fried, and so forth as appropriate for the product. The pancakes, doughnuts, hush puppies, batter, and crepes may also be prepared with any desired combinations of conventional ingredients including but not limited to other flours, extenders, binders, fillers, preserving agents, sweeteners, flavorings, seasonings, eggs, milk, nuts, and so forth.

In yet another embodiment, the pancake batter described above can be used to make a product such as dumplings from amaranth flour, water, oil and a small amount of salt (optional), and any conventional leavening agent. Process for combining ingredients and preparation are as follows. Teaspoon sized portions of batter are dropped into rapidly boiling thickened water for 2-6 minutes, preferably 5 minutes.

In yet another embodiment, a product such as waffles can be prepared from amaranth flour, water, oil, and small amounts of salt (optional), sweeteners (optional), and any conventional leavening agent in proportions ranging from 4 : 1 : ½ to ½ : 1 : 0. The ranges of general proportions are identical to that for corn bread, with preferred proportions being 1.6 : 1 0.15. Processes of combining ingredients and batter preparation are as described for cornbread. Batter is then placed in waffle irons or other type of molds and heated by conventional means.

In another embodiment a product such as french toast batter can be prepared from amaranth flour, water, oil, and uncooked, proteinaceous material, and a small amount of salt (optional) in proportions ranging from 1 : 14 : 8 : 8 to 1 : ½ : 0 : 0 by weight, preferably 1 : 4 : 1 : 2 in processes of gelatinizing the flour and water mixture, combining with remaining ingredients and blending with high speed blending equipment until smooth and homogeneous. Material to be coated and prepared for french toast is preferably amaranth bread, although any other bread or bread-like product may be used, and cooking is by any accepted technique.

Alternatively batter may be prepared by the method above omitting the step of gelatinizing the flour-water mixture. Alternatively, the proteinaceous material may be omitted, and the flour water mixture combined in ratios of 1 : 1 to 30 : 1, preferably 13 : 1, and heated to a gelatinized mixture useful as a batter. The batter may be used alone, or in combinations with bread crumbs and many other coating materials. The batter may also be prepared with any desired combinations of conventional ingredients including but not limited to other flours, extenders, binders, fillers, preserving agents, sweeteners, flavorings, seasonings, eggs, milk, nuts, and so forth.

In another embodiment, a product such as cookies can be prepared from amaranth flour, water, oil, small amounts of salt (optional), sweeteners (optional), and small amounts of any conventional leavening agents in proportions ranging from 4 : 1 : 0 to 0.5 : 1 : 2, by weight, preferably 2.5 : 1 : 0.4 in processes of mixing, kneading, shaping, baking to produce cookies. Baking conditions range from 275–500 F., preferably 8–10 minutes.

Alternatively, add toppings as desired to the unbaked or baked dough. Any desired fruit, nuts, flavors, seasonings, sweeteners of the conventional art may be incorporated. The cookies may also be prepared with any desired combinations of conventional ingredients including but not limited to other flours, extenders, binders, fillers, preserving agents, sweeteners, flavorings, seasonings, eggs, milk, nuts, and so forth.

In yet another embodiment, crackers may be produced in any suitable machine for mixing heavy doughs through processes involving combining flour, water, and oil in proportions ranging from 6 : 1 : 4 to ½ : 1 : 0, preferably 2½ : 1 : ⅓ parts flour, water, and oil and small amounts of salt and leavening agents. In processes including but not limited to molding, rolling, cutting, and extruding, shape dough into desired cracker shapes. Dough may or may not be coated with a thin film of oil and salt. Any conventional heating method may be used, preferably 350 F. for 20 minutes. The crackers may also be prepared with any desired combinations of conventional ingredients including but not limited to other flours, extenders, binders, fillers, preserving agents, sweeteners, flavorings, seasonings, eggs, milk, nuts, and so forth.

In another embodiment of the invention a product such as tortillas or chips can be prepared by blending amaranth flour with water, and then baking or frying the appropriately shaped dough. In preparing the mixture a range from ½ : 1 to 4 : 1 amounts of flour and water are blended, preferably 1.6 to 1 flour and water. The dough may be cooked by any desired means including but not limited to frying with or without oil, and baking with or without a thin film of oil, following the conventions of the art.

In still another embodiment of the invention, a food product such as pie crust is prepared by blending amaranth flour and oil in relative amounts of 0.4 : 1 to 1½ : 1 parts water per unit part flour, preferably 1 : 2½ parts water per one part flour, and 0.1 : 1 to 1 : 1 parts oil per unit part flour, preferably 0.4 parts oil per one part flour. Once the blend is prepared, it is kneaded, shaped or molded and baked if desired at temperatures ranging from 275 to 500 F., preferably 350 F. for from 2 to 45 minutes, preferably 10 minutes.

In yet another embodiment, doughs from processes described earlier for pie crust and pasta may be used to produce a puffed product by shaping the dough into flat, thin waters and frying the wafers in hot oil to produce a puffed or popped product. The dough may be shaped into a water of any other shape desired by combinations of extruding or other shaping means, rolling, cutting and other techniques in any order in any desired combination and fried. By this method shapes of a 'chip' or 'fry' may be obtained. Also long pieces may be shaped into a pretzel-like shapes and fried.

A puffed product may also be obtained when amaranth flour is combined with pureed, cooked amaranth. Although almost any desired combination may be used ranging from 5–100% flour, 0–95% cooked, and p, 0–50% water, the ratios for pie crust combined with an added 20% cooked pureed amaranth is preferred. Either of the above processes may be used to produce very small-sized ⅛"–1" wafers, flakes and granules which can be used as a cereal product. Although for hypoallergenic purposes the above is preferred, any combination of flours, other tubers, other powdered vegetable material, extenders, binders, fillers, adhesives, antioxidants, preservatives, sweeteners, flavorants, spices and the like may be used with the above process.

In yet another embodiment of the invention, pretzels may be prepared from the doughs described for tortillas, chips, and pie crusts in processes of shaping, optional salting, and various combinations of baking with or without a thin coat of oil, frying, broiling, steaming, drying common in the food art to produce a pretzels of desired sizes and shapes. Additional embodiments include the pretzels above to which have been added to dough before baking or to the outside surface before or after baking, a variety of fillers, extenders, binders, flavorings, seasonings, preservatives and the like common to the art.

In yet another embodiment, the thick dough produced by the processes described in the preparation of pie crust may be used to produce dough encased or wrapped food products. The kneaded, thoroughly mixed dough may be shaped by extruding, rolling, cutting, and any other convenient technique to produce a variety of shapes onto which pureed fruit, chopped meats, hot dogs, meat and vegetable combinations, cheese and the like may be placed. For example the thick dough may be shaped into 3 ×3 × ¼ inch squares onto which a pureed fruit such as sapote or carambola, and any other unusual or common fruit, are placed. These may be baked, broiled, or fried as is or 2 squares may be placed together such that the fruit forms a middle or inside layer in a sandwich-type effect. This may be baked, broiled, or fried to produce a product or may be frozen for sale to the consumer as a frozen product.

In another example, conventional art may be used to completely encase meat and vegetable mixtures. The dough covered product which may have any shape, commonly an ovoid shape ranging from 1 inch to 6 inches in length may be baked, boiled, broiled, fried and so forth in any conventional means to produce good tasting, convenient foods.

The dough may also be used in pot pie-type products.

In another example, pureed or flaked meat may be combined with a small amount of imitation mayonnaise in approximate proportions of 2 : 1 and placed on a 6×6×¼ inch dough square. The dough is rolled around the meat mixture to form a tamale-like shape. This product may be baked, broiled, fried, or frozen. If uncooked meats are used, the product should be cooked by means other than frying. The dough-wrapped products may also be prepared with any desired combinations of conventional ingredients including but not limited to other flours, extenders, binders, fillers, preserving agents, sweeteners, flavorings, seasonings, eggs, milk, nuts, and so forth.

In another embodiment, amaranth flour may be combined with a vegetable oil such as corn oil, olive oil, or the like in an amount ranging from 1:2 to 1:4 parts by weight oil per part by weight flour, preferably 1:2, in processes to produce a product very similar to peanut butter in taste and consistency. In an additional embodiment this flour-oil mixture may be partially gelatinized to produce a product that will hold oil in the suspension more effectively.

The flour may be combined with various ingredients to prepare a colloidal product having the consistency of mayonnaise. Flour, water, and oil are combined in ratios of 0.5-3 : .2-6 : 1/5-10, preferably in ratios of 1:1.2:1.4. The flour and ¼ to all of the water, preferably all of the water are combined and heated by any convention of the art to such temperature and for sufficient time to completely gelatinize the starch granules. This mixture in steps of cooling (optional) and high speed blending with remaining water, oil, and flour to produce a colloidal product to which may be added any acid, such as lemon juice, citric acid, ascorbic acid, acetic acid and the like in amounts ranging from 0-2 parts acid to 1 part original flour used, about 0.2:1 is preferred.

In either product, the mayonnaise has the colloidal properties of mayonnaise, with no other added ingredients. This is not to preclude the use of other ingredients commonly used in the food art, including but not limited to eggs, milk, other flours and starches, sweeteners, flavors, seasonings, and spices of any kind.

The mayonnaise produced by the above processes has the advantages of being able to be frozen and thawed without destroying or significantly altering the colloidal properties of the product.

In another embodiment of the invention, a product such as a pudding can be prepared by blending flour, water, and oil in proportions ranging from 1 : 10 : 6 to 1 : ½ : 1/10, preferably about 1 : 3 : 0.36. The product is produced in processes where the flour and water are heated by any convention of the art to produce a thick gelatinized paste. This paste is then combined with the remaining raw materials and blended to a smooth, homogeneous, mixture by conventional mixing techniques. With the addition of no additional ingredients the product has a sweet, pleasant taste. However, this is in no way intended to preclude the use of other constituents commonly used in puddings including but not limited to any desired combinations of conventional ingredients including but not limited to other flours, extenders, binders, fillers, preserving agents, sweeteners, flavorings, seasonings, eggs, milk, nuts, and so forth.

In still another embodiment of the invention, when a given amount of amaranth flour is mixed with water of a temperature range from 0 to 150 degrees C., boiling water is preferred in proportions ranging from ½ to 4 parts of flour per part water, preferably 1½ parts flour to one part water, a dough can be prepared, which, after maintaining a heating and kneading period of from 0 to 10 minutes, preferably 1 minute, followed by extruding, cutting and drying, prepares such products as noodles, pastas and the like. It is also possible to mix the batter prepared with other vegetable matter in the amounts to produce stiff doughs for gnocci, hard dumplings, and other pasta products. In another embodiment of the invention, a thick gelatinized paste of cooked amaranth flour and water comprised of preferably 2 : 1 parts flour and water, with acceptable ranges of 2 : 1/10–10, may be added to the above described dough mixture before extrusion to any desired pasta shapes, to produce substitutes for egg based pasta.

In a further embodiment of the invention, the pasta doughs described above, with or without the egg-substitute may be heated at temperatures above 50 C. for 2–30 minutes, preferably 2–5 minutes at 95 C. to gelatinize a part of all of the dough prior to extrusion.

The pastas thus described are dried by any conventional means, preferably air dried on trays to produce a final product.

In its final uses, this pasta does not swell significantly beyond its dried size, when cooked in boiling water and the like. This is due to the high fiber content which has been retained in the flour. These fibers prevent the typical swelling and conversion to a jelly-like mass common to noodles from most pure starches. Thus these pasta products retain a form and consistency similar to wheat based noodle products. They may be used in all ways any other noodles ar formed.

In another food embodiment, the amaranth flour can be combined with water in a ratio of 12 : 1 to 3 : 1 parts by volume water per unit volume of flour, preferably 6.5:1 water to flour, and a small amount of a vegetable oil to produce a amaranth milk. Preferably half of the flour and water are combined (actual amounts may range from 10–80% flour and 25–100% water), heated by conventional methods until the mixture is completely gelatinized. The gelatinized mixture and remaining ingredients are combined, thoroughly mixed in a high speed blending device to produce a amaranth milk or other similar fluid mixtures.

In the above embodiment, flour of almost any particle size may be used ranging from very coarse to very fine. The particle size is not important for that portion of the flour used for gelatinization, although fine flours are preferable. A more finely divided flour product is desired for the flour that remains uncooked in the milk. The smaller the particle sizes, the better, preferably at least less than 0.001 inch. The milk produced from very fine flours does not require straining to yield a smooth homogeneous product. Larger particle sizes produce a gritty product that must be strained before use. The larger the particle sizes, the greater proportion of amaranth flour that is removed by straining, and the more separation into layers that occurs on setting.

In another food embodiment, amaranth flour can be combined with water in a ration of 1 : 1 to 30 : 1 parts by volume of water per unit of flour, preferably 3–6:1 water to flour, and a small amount of a vegetable oil. 50 to 100 per cent of the flour is combined, and heated until the mixture is completely gelatinized. The gelatinized mixture and remaining ingredients are combined, thoroughly mixed in a high speed blending device to produce substitutes for light to heavy creams and condensed milk.

In other embodiments of the invention, the finely divided flour may be employed as a thickener, filler, or extender in the preparation of hypoallergenic cosmetics, and industrial products. For example, amaranth flour of fine particle sizes may be used in dusting powders and face powders. Various shades may be obtained by heating and toasting methods. This produces a face powder product which could be well tolerated because people would be only placing nonallergic items on their faces. Similar powders may also be used as bases for liquid and paste makeups to produce hypoallergenic products. The cosmetic preparations may also be prepared with any desired combinations of amaranth flour with conventional ingredients including but not limited to other flours, extenders, binders, fillers, preserving agents, and so forth.

The cooked amaranth flour may also be used in combination with the raw amaranth flour in many of the products and processes described previously, and may also be used with many other types of flours.

Yet another embodiment involves processes to produce an infant formula. Many infants are unable to tolerate the currently available infant formulas. Infants unable to tolerate the grains, legumes, milk products, eggs, and grain-derived sugars listed earlier along with coconut oil are almost certainly going to be intolerant of all commercially available infant formulas. These infants are usually unable to tolerate breast milk because of allergies to digested food residues in the milk. The parents of these infants desperately seek alternatives and usually end up using cooked purees of tubers and other foods. There is a real need for infant formulas without grains, grain-based sugars, legumes, milk and milk products, and coconut or corn oil, and a wider variety of products.

The earlier described process for producing amaranth milk, in which finely powdered, precooked, dried amaranth flour is substituted for the raw flour in thy second step of the process ma be used to produce infant formulas. In one infant formula embodiment the just described formula is used without further modification in either full fluid form, condensed form, or dry powdered form as a formula to which the user would add pureed, cooked protein in the desired amount of protein and fat. This would be ideal for many infants since the protein and fat sources could be varied by the parents according to the physician's instructions and specific allergies of the infant. This would assure the broadest tolerance of the formula.

In another embodiment of the invention, a more complete infant may be obtained by adding the previously described amounts of protein and carbohydrates to the above described formulas. By conventions of the art formula available as ready-to-feed, liquid concentrate, and dry powder, and any other form are included in the embodiment.

Many variations in the above formula by varying amounts of oil, water, amaranth, cooked versus uncooked flours, added ingredients and so forth, all are hereby included in the embodiment. The infant formula ma also be prepared with amaranth flour and combinations of conventional ingredients including but not limited to other flours, extenders, binders, fillers, preserving agents, sweeteners, flavorings, seasonings, eggs, milk, nuts, and so forth. These are hereby included in the embodiments.

In another embodiment, amaranth flour may be used in a wide variety of pharmaceutical products as a filler, extender, and inert ingredient. The use of a material for these purposes would eliminate allergic reactions that food allergic patients may have to the nonactive ingredients, would thereby enhance the number of persons who tolerate the drugs and could help the medications to be more effective for the allergic patient.

Many of the products described above are well suited for the preparation of packaged dry mixes, frozen products and the like, all such products and processes are incorporated with this embodiment.

As is evident from the above discussion, the central objective of the present invention is to provide a variety of different foodstuffs, the basis for all of which is a plant, which is well tolerated by many persons with multiple allergies, hence the term hypoallergenic. Thus, insofar as the flour obtained is mixed with other ingredients which do not detrimentally affect the hypoallergenic properties of the food product obtained, hypoallergenic foodstuffs of different sorts can be obtained by the techniques described above. On the other hand, it is recognized that other ingredients can be added to the flour used in the present invention which may destroy the hypoallergenic nature of the food-stuff being produced, but yet which produce useful foodstuffs of still different qualities. The present invention also embraces these hyperallergenic foodstuffs, and therefore the present invention is not limited to just hypoallergenic foodstuffs.

Having generally described this invention, a further understanding can be obtained by reference to certain specific examples which are provided herein for purposes of illustration only and ar not intended to be limiting unless otherwise specified.

EXAMPLE NUMBER 1

AMARANTH BREAD

Place 560.4 g amaranth flour in a suitable conventional mixing device. Slowly add 226.5 g water, 3.25 g salt, and 100 g oil while mixing at lowest speed. When well blended mix, at highest speed for about 1 minute. Stir in 47 g baking powder; then mix at high speed for 15 seconds. May need to knead dough with hands, will be very stiff. Carefully place in oven heated to 425 F. and bake for 35 minutes. The amount of water needed varies with the moisture content and particle size of the flour. More coarse flour and/or flour with a lower moisture content will require more water. The resultant amaranth bread product may be used in any way wheat bread is used.

EXAMPLE NUMBER 2

AMARANTH IMITATION CORN BREAD

Ingredients: 560.4 g amaranth flour, 226.5 g water, 47 g amaranth baking powder, 3.25 g salt, 100 g oil. Combine above ingredients with baking powder added last; mix well, at highest speed with conventional mixing equipment until well blended and uniform consistency, about 1 minute. Transfer quickly into suitable baking container and bake 20–25 minutes at 425 F.

Alternatively, the following proportions may be used in an imitation corn bread with honey or other liquid sweetener: 560.4 g amaranth flour, 226.5 g water, 3.25 g salt, 75 g honey, 47 g amaranth baking powder, 50 g oil.

EXAMPLE NUMBER 3

CAKE DOUGH 560.4 g amaranth flour, 226.5 g water, 90 g honey, 35 g oil, 47 g suitable leavening agent, may be combined in the processes described in Example 2. Dough may be baked as described in Example 2, prior to baking or after, the cake dough may be prepared or finished with any desired combinations of conventional ingredients including but not limited to other flours, extenders, binders, fillers, preserving agents, sweeteners, flavorings, seasonings, eggs, milk, nuts, and so forth.

EXAMPLE NUMBER 4

AMARANTH MUFFINS

Combine 560.4 g amaranth flour, 226.5 g water, 3.25 g salt, 100 g oil, and mix well, at high speed with conventional techniques of the art until smooth and well blended. Add 47 g baking powder and mix well. Pour quickly or transfer by other means into suitable baking equipment. Bake for 20–35 minutes at 425 F.

EXAMPLE NUMBER 5

AMARANTH PANCAKES

The following ingredients: 280.3 g amaranth flour, 226.5 g water, 6.5 g salt, 50 g oil, 16 g amaranth baking powder, are combined and mixed well on highest speed, preferably 1–2 minutes in high speed blending device. Batter may be transferred to suitable baking or frying device, device to be prepared as required by the art, preheated on medium-high heat. Dough may be cooked in sizes ranging from dot sizes to several feet across. Turn when top surface has turned dull and the bottom surface is golden brown in color.

When honey or other liquid sweetener is used, the ingredients: 280.3 g amaranth flour, 226.5 g water, 6.5 g salt, 37.5 g honey, 25 g oil, 16 g amaranth baking powder, may be used in the process described above.

EXAMPLE NUMBER 6

AMARANTH PANCAKE MIX

To provide an example of a dry mix-type product, amaranth pancake mix is used. A amaranth pancake mix product can be made by combining ingredients: 560.4 g flour, 8.7 g salt, and 10.7 g amaranth baking powder. Mix ingredients well in a rolling ball mill or other conventional means to form a dry mix. Pancakes can be made from this dry mix by the addition of water and water/oil mixtures.

Alternatively, by conventions of the art, the pancake mix oils may also be added to the above ingredient mix to produce a dry mix that contains oils. Also, sweeteners, flavors, seasonings, binders, fillers, and so forth may be utilized in the production of amaranth pancake mixes.

EXAMPLE NUMBER 7

AMARANTH WAFFLES

The following ingredients are combined by the method described above in Example 5: 140.1 g amaranth flour, 85 g water, 16 g salt, 12.5 g oil, 4 g amaranth baking powder. Pour batter into waffle iron or other suitable molding or shaping device preheated to 300–500 F. Watch for steam coming from the waffle iron as the waffles cook. Leave waffle iron closed as long as steam can be seen rising from the waffle iron. When steam stops, all water has been baked out of the batter and waffles are done, 5–10 minutes or more. When done the waffles should be golden brown in color.

EXAMPLE NUMBER 8

AMARANTH FRENCH TOAST

Combine 52.6 g flour, 3.25 g salt, and 226.5 g water and mix until smooth and homogeneous. Heat by any desired convention until mixture is well gelatinized and thickened. Stir in 50 g oil. Pour mixture into high speed blending device; while blending at high speed, slowly drop in ground meat or other protein source and blend until meat is completely pulverized and liquefied, or cook 226.5 g water and 17.5 g flour by any conventional method until gelatinized.

Coat pieces of amaranth bread. Fry to slightly browned and crusty in lightly greased griddle or skillet preheated to medium high. Alternatively french toast batter may be prepared by the method as described above without cooking the flour/water mixture.

French toast batter may be used for many combinations with amaranth bread crumbs and many other coating materials or alone.

EXAMPLE NUMBER 9

AMARANTH COOKIES

Combine and mix well by the conventional art: 560.6 g amaranth flour, 226.5 g water, 1.6 g salt, 100 g oil, 16 g amaranth baking powder. Form into cookie shapes by the conventional art. Bake at 350 F. on ungreased surface for 10–15 minutes, or until a light golden brown on the underside. Alternatively, add toppings as desired to the unbaked or baked dough. Any desired fruit, nut, flavors, seasonings of the conventional art may also be used.

When a liquid sweetener or honey is used, the following ingredients are combined as described above: 560.6 g amaranth flour, 226.5 g water, 6.5 g salt, 75 g honey, 50 g oil, 16 g amaranth baking powder.

EXAMPLE NUMBER 10

AMARANTH DOUGHNUTS, PRETZELS, HUSH PUPPIES, DOUGHNUT HOLES

From batter prepared in the method of Example 5, extrude batter through a doughnut press or any other desired device in rings onto hot oil; batter may also be dropped in balls, long pieces, even pretzel shapes. Temperature of the oil should be about 300–500 degrees.

If the oil is hot enough the dough will float at the top of the oil. Fry doughnuts or other shapes until golden brown on all sides. Remove from oil, drain. Serve plain or top with fruit, honey, nuts, coconut, peanut butter, etc.

Alternatively, doughnuts may be preparations of conventional ingredients including but not limited to: other flours, extenders, binders, fillers, preserving agents, flavorings, seasonings, eggs, milk, and so forth.

EXAMPLE NUMBER 11

AMARANTH DUMPLINGS

Combine 140.1 g amaranth flour, 56.8 g water, 16 g amaranth baking powder, and 50 g oil, until smooth and creamy. Let dough set for about 15 minutes. Drop teaspoon-sized portions of batter into about 2 liters of rapidly boiling water or broth, may be thickened. Allow to remain in boiling water 1-2 minutes, preferably 1½ minutes. If dumplings remain in boiling broth longer, dumplings will dissolve. When done, dumplings will be light and tender on the inside.

EXAMPLE NUMBER 12

AMARANTH BATTER

A batter prepared by the method of Example 5 may be used as batter for deep frying and for fondue cooking techniques. Coat vegetables, fruit, or cooked meat in batter and deep fry in hot oil (preheated to medium-high heat). If the oil is hot enough the dough should float at the top of the oil. Test for proper temperature with a small ball of dough.

EXAMPLE NUMBER 13

CREPES

In yet another embodiment of the batter prepared in Example 5, the batter may be used to make a crepe-like product. The batter may be diluted by the addition of 10-400 g water, preferably 100 g to make a crepe-like product. The batter is spread in very thin layers on a cooking surface, and prepared according to the accepted convention.

EXAMPLE NUMBER 14

AMARANTH PIE CRUST

Mix thoroughly, 140.1 g amaranth flour, 50 g oil, 56.8 g water. Shape into round, flat dough ball. By any conventional means, shape into appropriate dimensions for pie crust. Preferably, place between cellophane or wax paper sheets before rolling out dough. This dough is also very well suited to shaping in a mold; it can be reshaped many times without becoming hard and leathery.

Amaranth pie crust may be used as a double or single crust pie, with any type of filling, including meat (e.g., chicken pot pie) or fruit filling. May be used baked or unbaked. For a baked pie crust, bake for 10 minutes at 350 F.

Although above ingredients is preferred, amaranth flour may be used with shortening or lard and any other conventional ingredients. For example, when using lard, use about 100 g and decrease water to 10-14 g. Dough will see stiff and hard, but will be just right after baking.

EXAMPLE NUMBER 15

AMARANTH TORTILLAS, CHIPS

Mix 140.1 g amaranth flour with 85.2 g water; knead until well blended and very thick. By any desired conventional means achieve the shapes and sizes of tortillas or chips. May be fried with or without oil, or baked. When fried without oil, heat on medium high heat until slightly browned on both sides; turn as needed. When fried in hot oil, fry until crisp. Alternatively, bake by conventional means until crisp.

EXAMPLE NUMBER 16

PRETZELS

Doughs produced by the processes described in Examples 14 and 15 may be used in processes of shaping to form pretzels of various sizes, coating with oil (optional), cooking by various processes of the art including but not limited to baking, frying, and drying to produce pretzels of varying sizes.

In alternative processes, pretzels may be produced in processes above into which are incorporated any combinations of processes including but not limited to additional flours, eggs, milk, flavorings, seasonings, binders, fillers, extenders, and preserving agents.

EXAMPLE 17

AMARANTH IMITATION NUT BUTTER 560.4 grams of amaranth flour are placed into any blending equipment suitable for mixing very thick doughs at very high speeds, to which is added 150-200 g edible fatty material, such as vegetable oils (preferred for hypoallergenic products) but could also include other fatty materials. The materials are intimately mixed for about 2 minutes or until the entire mixture is well blended, and the consistency of peanut butter. After several weeks of storage oil and flour will begin to separate, but is recombined very easily. Alternatively, the mixture may be heated until the amaranth flour is partially gelatinized to produce an imitation nut butter that separates less easily.

EXAMPLE 18

AMARANTH IMITATION MAYONNAISE

Combine 140.1 g amaranth flour, 3.25 g salt, and 170.4 g cold water in a pan and heat until thick while maintaining temperature at 50 to 150 C., until mixture is completely gelatinized and thickened. Place mixture in conventional high speed blending device; add 200 g oil, (optional: 21.3 g lemon juice, vinegar, or ascorbic acid solution). Mix materials on highest speed until well blended, smooth, and uniform consistency. Mayonnaise will thicken as it cools.

Alternatively an imitation mayonnaise product may be prepared using flour, oil, and water combinations only.

EXAMPLE NUMBER 19

AMARANTH MILK

Combine 906 g water and 140.1 g amaranth flour, 12.5 g oil. Blend together in any high speed blending device. Blend 1-30 minutes at highest speeds, preferably 4 minutes. May be strained if flour not sufficiently fine.

EXAMPLE NUMBER 20

AMARANTH NOODLES

Using conventional equipment for kneading thick dough, combine 560.4 g flour and 226.5 g water. Knead well until dough is well mixed and forms soft doughy clumps. Extrude to various shapes of macaroni, fettucine, spaghetti, lasagna and the like. Cut to desired lengths, dry by any conventional means, preferably air drying on trays, conveyors or the like. Dough may be used to make any pasta product common in the art including but not limited to ravioli, Chinese-style meat filled noodle dumplings, and other meat-filled products.

Alternatively a small amount of flour and water, preferably 20 g amaranth flour and 120 g water may be cooked to a thick paste and added to the above mixture.

In another alternative process, prior to extruding, the flour mixture described above which may or may not be simultaneously kneaded, may be maintained at temperatures above 50 C. for 2-30 minutes, preferably 2-5 minutes at 95 C. to gelatinize part of all of the dough.

When cooking, immerse noodles in boiling water for 2-10 minutes depending on width of noodles. Any other cooking techniques of the art may also be used. Noodles will change from off-white opaque to light brown as the starch granules gelatinize. Noodles may be used in any type pasta dish—soups, stews, pasta and sauce dishes, and the like.

EXAMPLE NUMBER 21

AMARANTH CRACKERS

In any suitable machine for mixing heavy doughs, combine 560.4 g amaranth flour, 226.5 g water, 6.5 g salt, 75 g oil, and 23.6 g baking powder. By any conventional means, including but not limited to molding, rolling, cutting, extruding, and the like, shape into desired shapes. Coat with a very thin film of oil, sprinkling with salt. Heat to 350 F. for 20-25 minutes. Otherwise, cook by any convention of the art, including baking, frying and the like.

Alternatively, omit oil, or oil and salt, increasing water by 30 grams.

Alternatively, use binders, flours, sweeteners, extenders, flavorings, seasonings, fillers and other ingredients common to the art to produce a hyperallergenic cracker.

EXAMPLE 25

PUDDING

Combine 226.5 g water, 70.1 g flour—cook in any conventional heating apparatus until mixture is gelatinized. Put in a high speed blender and blend until very smooth, about 5 minutes. Add 25 g oil, cool.

EXAMPLE NUMBER 23

AMARANTH FLOUR

Pulverize amaranth seeds by any desired technique or combination of techniques common to the art to produce a meal. The meal is further ground, in as many repetitions and by such techniques as needed to pulverize the meal to a uniform, fine particle size with preferably all particles remaining in the flour.

EXAMPLE 24

COOKED AMARANTH FLOUR 100 g amaranth seed, meal, or flour is combined with 1000 g water and heated to about 200 F. for about 4 hours, with water added as necessary to form a soft, gelatinized mass. The mass is subjected to methods of pureeing, pulping, comminuting, pulverizing and the like to form a smooth, homogeneous fluid or paste. This mixture is dried by suitable means of the art and pulverized to form a fine powder.

Having now fully described the invention, it will be apparent to one of ordinary skill in the art that many changes and modifications can be made thereto without departing from the spirit of the invention as set forth herein.

What is claimed as new and so intended to be secured by letters patent is:

1. An edible flour of amaranth seeds of family Amaranthaceae, wherein the flour consists of the entire amaranth seed, including all of the starch and fiber portions of said amaranth, comminuted to a size so that said entire comminuted amaranth seed will pass through a screen of 0.02 inch mesh, said flour having a moisture content of less than 20% by weight.

2. An edible amaranth flour possessing the ability to maintain a risen structure in the absence of other grain flours, legume flour, or added fiber, said edible flour consisting of comminuted particles of entire amaranth seeds including substantially all of the starch and fiber content of the amaranth seeds, comminuted to a size so that all of said particles pass through a screen of 0.02 inch mesh, wherein said flour has a moisture content of less than 20% by weight.

3. The entire flour of claim 2 wherein the entire amaranth flour passes through a screen of 0.001 inch mesh.

4. The flour of claim 2 wherein the amaranth flour is uncooked.

5. The four of claim 2 wherein the amaranth flour is at least partially gelatinized.

6. A baked product consisting essentially of, amaranth flour, water, and leavening agent, wherein the amaranth flour consists of the flour of claim 2, and wherein the flour is present in an amount of 1 part by weight, and the water is present in an amount of 0.1–4 parts by weight per weight of flour.

7. A colloidal product consisting essentially of, amaranth flour, oil, and water, wherein the amaranth flour consists of the flour of claim 2, and wherein the flour is present in an amount of 0.5–3 parts by weight, the water is present in an amount of 0.2–6 parts by weight, and the oil is present in an amount of 0.2–10 parts by weight.

8. A fired product consisting essentially of amaranth flour, oil, and water, wherein the amaranth flour consists of the flour of claim 2.

9. An extruded product consisting essentially of amaranth flour and water, wherein the amaranth flour consists of the flour of claim 2.

10. A milk substitute consisting essentially of amaranth flour and water, wherein the amaranth flour consists of the flour of claim 2, and wherein the flour and water are present in proportions of 1:3 to 1:12 parts by weight of flour per weight of water.

11. An ice cream substitute formed by the process consisting essentially of the steps of freezing the milk substitute of claim 10.

12. An infant formula consisting essentially of amaranth flour and water, wherein the amaranth flour consists of the flour of clam 2.

13. An imitation nut butter product consisting essentially of amaranth flour and oil, wherein the amaranth flour consists of the flour of claim 2.

14. A batter-type product consisting essentially of, amaranth flour, oil, and water, wherein the amaranth flour consists of the flour of claim 2, and wherein the flour is present in an amount of 1 part by weight, the water is present in an amount of 0.25–2 parts by weight, and the oil is present in an amount of 0–0.5 part by weight.

15. A method of making an edible amaranth flour having a particle size of less than 0.02 inch mesh and a moisture content of less than 20% by weight, which method consists essentially of the steps of, (a) comminuting the seed, (b) retaining substantially all of the starch and fiber content of the seed, and (c) recovering an edible flour product of amaranth seeds having a particle size diameter of at least less than 0.02 inch, and a moisture content of less than 20% by weight.

16. An edible flour of quinoa seeds of family Chenopodiaceae, wherein the flour consists of the entire quinoa seed, including all of the starch and fiber portions of said quinoa, comminuted to a size so that said entire comminuted quinoa seed will pass through a screen of 0.02 inch mesh, said flour having a moisture content of less than 20% by weight.

17. An edible quinoa flour possessing the ability to maintain a risen structure in the absence of other grain flours, legume flour, or added fiber, said edible flour consisting of comminuted particles of entire quinoa seeds including substantially all of the starch and fiber content of the quinoa seeds, comminuted to a size so that all of said particles pass through a screen of 0.02 inch mesh, wherein said flour has a moisture content of less than 20% by weight.

18. The entire flour of claim 17, wherein the entire quinoa flour passes through a screen of 0.001 inch mesh.

19. The flour of claim 17, wherein the quinoa flour is uncooked.

20. The flour of claim 17, wherein the quinoa flour is at least partially gelatinized.

21. A method for making an edible quinoa four having a particle size of less than 0.02 inch mesh and a moisture content of less than 20% by weight, which method consisting essentially of the steps of, (a) comminuting the seed, (b) retaining substantially all of the starch and fiber content of the seed, and (c) recovering an edible flour product of quinoa seeds having a particle size diameter of at least less than 0.02 inch, and a moisture content of less than 20% by weight.

* * * * *